(12) United States Patent
Muller et al.

(10) Patent No.: US 6,518,281 B2
(45) Date of Patent: Feb. 11, 2003

(54) IMMUNOTHERAPEUTIC AGENTS

(75) Inventors: George W. Muller, Bridgewater, NJ (US); Mary Shire, North Plainfield, NJ (US)

(73) Assignee: Celgene Corporation, Warren, NJ (US)

( * ) Notice: Subject to any disclaimer, the term of this patent is extended or adjusted under 35 U.S.C. 154(b) by 0 days.

(21) Appl. No.: 09/909,506

(22) Filed: Jul. 20, 2001

(65) Prior Publication Data

US 2002/0002188 A1 Jan. 3, 2002

Related U.S. Application Data

(63) Continuation of application No. 09/366,985, filed on Aug. 4, 1999, which is a division of application No. 09/007,135, filed on Jan. 14, 1998, now Pat. No. 5,968,945, which is a continuation of application No. 08/520,710, filed on Aug. 29, 1995, now Pat. No. 5,728,845, and a continuation of application No. 08/578,738, filed on Dec. 26, 1995, now Pat. No. 5,728,844, which is a continuation-in-part of application No. 08/520,710.

(51) Int. Cl.$^7$ .................... C07D 275/06; C07D 417/00; C07D 513/00; C07D 253/02; A61K 31/44

(52) U.S. Cl. .................. 514/300; 514/301; 514/303; 514/373; 514/397; 514/421; 546/113; 546/114; 546/118; 548/210; 548/211; 548/302.7; 548/404; 548/453

(58) Field of Search .................... 514/373, 300, 514/301, 303, 397, 421; 548/210, 211, 302.7, 404, 453; 546/113, 114, 118

Primary Examiner—Bruck Kifle
(74) Attorney, Agent, or Firm—Mathews, Collins, Shepherd & McKay, P.A.

(57) ABSTRACT

Novel amides and imides are inhibitors of tumor necrosis factorα and phosphodiesterase and can be used to combat cachexia, endotoxic shock, retrovirus replication, asthma, and inflammatory conditions.

9 Claims, No Drawings

IMMUNOTHERAPEUTIC AGENTS

CROSS-REFERENCE TO RELATED APPLICATIONS

This is a continuation of Ser. No. 09/366,985 filed Aug. 4, 1999, which is a divisional of Ser. No. 09/007,135 filed Jan. 14, 1998, now U.S. Pat. No. 5,968,945 which is a continuation of both (1) Ser. No. 08/520,710 filed Aug. 29, 1995, issued as U.S. Pat. No. 5,728,845; and (2) Ser. No. 08/578,738 filed Dec. 26, 1995, issued as U.S. Pat. No. 5,728,844, the disclosures of which are incorporated herein by reference. Ser. No. 08/578,738 is a continuation-in-part of Ser. No. 08/520,710.

BACKGROUND OF THE INVENTION

This invention relates to a method of reducing the level of cytokines and their precursors in mammals and to compounds and compositions useful therein.

In particular, the invention pertains to a class of compounds which inhibit the action of phosphodiesterases, particularly PDE III and PDE IV, and the formation of TNFα and $NF_\kappa B$. In a first embodiment, the compounds of the present invention can be diagrammatically represented by the formula:

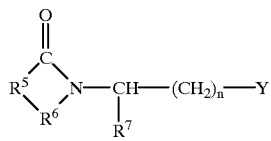

in which:
$R^5$ is:
(i) the divalent residue of pyridine, pyrrolidine, imidizole, or thiophene, wherein the two bonds of the divalent residue are on vicinal ring carbon atoms;
(ii) a divalent cycloalkyl of 4 to 10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl or halo;
(iii) di-substituted vinylene, substituted with nitro, cyano, trifluoromethyl, carbethoxy, carbomethoxy, carbopropoxy, acetyl, carbamoyl, carbamoyl substituted with and alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, or halo; or
(iv) ethylene, unsubstituted or substituted with 1 to 2 substituents each selected independently from nitro, cyano, trifluoromethyl, carbethoxy, carbomethoxy, carbopropoxy, acetyl, carbamoyl, carbamoyl substituted with and alkyl of 1 to 3 carbon atoms, acetoxy, carboxy, hydroxy, amino, amino, substituted with an alkyl of 1 to 3 carbon atoms, alkyl of 1 to 4 carbon atoms, alkoxy of 1 to 4 carbon atoms, or halo;
$R^6$ is —CO—, —$CH_2$—, —$CH_2CO$—, or —$SO_2$—;
$R^7$ is
(i) cyclic or bicyclic alkyl of 4 to 12 carbon atoms;
(ii) pyridyl;
(iii) phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, straight or branched alkyl of 1 to 10 carbon atoms, straight or branched alkoxy of 1 to 10 carbon atoms, or halo;
(iv) benzyl substituted with one to three substituents each selected independently from the group consisting of nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 10 carbon atoms, or halo;
(v) naphthyl; or
(vi) benzyloxy;
Y is —COX, —C≡N, —$OR^8$, alkyl of 1 to 5 carbon atoms, or aryl;
X is —$NH_2$, —OH, —NHR, 13 $R^9$, —$OR^9$, or alkyl of 1 to 5 carbon atoms;
$R^8$ is hydrogen or lower alkyl;
$R^9$ is alkyl or benzyl; and,
n has a value of 0, 1, 2, or 3.

Within this group, Y is preferably —C≡N or —CO$(CH_2)_m$ $CH_3$ in which m has a value of 0, 1, 2, or 3; and In a second embodiment, the compounds of the present invention can be diagrammatically represented by the formula:

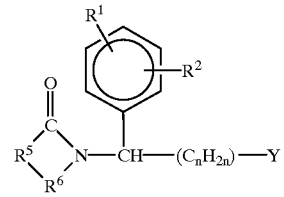

in which:
one of $R^1$ and $R^2$ is $R^3$—X— and the other is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkoxy, halo, or $R^3$—X—;
$R^3$ is monocycloalkyl of up to 10 carbon atoms, polycycloalkyl of up to 10 carbon atoms, or benzocyclic alkyl of up to 10 carbon atoms;
X is —$CH_2$— or —O—;
$R^5$ is:
(i) the vicinally divalent residue of pyridine, pyrrolidine, imidizole, or thiophene, wherein the two bonds of the divalent residue are on vicinal ring carbon atoms;
(ii) a vicinally divalent cycloalkyl of 4–10 carbon atoms, unsubstituted or substituted with 1 to 3 substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl;
(iii) di-substituted vinylene, substituted with nitro, cyano, trifluoromethyl, carbethoxy, carbomethoxy, carbopropoxy, acetyl, carbamoyl, carbamoyl substituted with and alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, or halo; or (iv) ethylene, unsubstituted or substituted with 1 to 2 substituents each selected independently from nitro, cyano, trifluoromethyl, carbethoxy, carbomethoxy, carbopropoxy, acetyl, carbamoyl, carbamoyl substituted with and alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, or halo;

$R^6$ is —CO—, —CH$_2$—, or —CH$_2$CO—;

Y is —COX, —C≡N, —OR$^8$, alkyl of 1 to 5 carbon atoms, or aryl;

X is —NH$_2$, —OH, —NHR, —R$^9$, —OR$^9$, or alkyl of 1 to 5 carbon atoms;

$R^8$ is hydrogen or lower alkyl;

$R^9$ is alkyl or benzyl; and, n has a value of 0, 1, 2, or 3.

The term alkyl as used herein denotes a univalent saturated branched or straight hydrocarbon chain. Unless otherwise stated, such chains can contain from 1 to 18 carbon atoms. Representative of such alkyl groups are methyl, ethyl, propyl, isopropyl, butyl, isobutyl, sec-butyl, tert-butyl, pentyl, isopentyl, neopentyl, tert-pentyl, hexyl, isohexyl, heptyl, octyl, nonyl, decyl, undecyl, dodecyl, tridecyl, tetradecyl, pentadecyl, hexadecyl, heptadecyl, octadecyl, and the like. When qualified by "lower", the alkyl group will contain from 1 to 6 carbon atoms. The same carbon content applies to the parent term "alkane" and to derivative terms such as "alkoxy".

The term cycloalkyl as used herein denotes a univalent saturated cyclic hydrocarbon chain. Unless otherwise stated, such chains can contain up to 18 carbon atoms. Monocyclicalkyl refers to groups having a single ring group. Polycycloalkyl denotes hydrocarbon systems containing two or more ring systems with two or more ring carbon atoms in common. Benzocycloalkyl signifies a monocyclicalkyl group fused to a benzo group.

Representative of monocycloalkyl groups are cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, and cyclooctadecyl. Representative of polycycloalkyl include bicyclo[2.2.1]heptyl, bicyclo[3.2.1]octyl, and bicyclo[2.2.2] octyl. Benzocycloalkyl is typified by tetrahydronaphthyl, indanyl, and 1.2-benzocycloheptanyl.

Tumor necrosis factor α, or TNFα, is a cytokine which is released primarily by mononuclear phagocytes in response to a number immunostimulators. When administered to animals or humans, it causes inflammation, fever, cardiovascular effects, hemorrhage, coagulation, and acute phase responses similar to those seen during acute infections and shock states. Excessive or unregulated TNFα production thus has been implicated in a number of disease conditions. These include endotoxemia and/or toxic shock syndrome {Tracey et al., Nature 330, 662–664 (1987) and Hinshaw et al., Circ. Shock 30, 279–292 (1990)}; cachexia {Dezube et al., Lancet, 335 (8690), 662 (1990)} and Adult Respiratory Distress Syndrome where TNFα concentration in excess of 12,000 pg/mL have been detected in pulmonary aspirates from ARDS patients {Millar et al., Lancet 2(8665), 712–714 (1989)}. Systemic infusion of recombinant TNFα also resulted in changes typically seen in ARDS {Ferrai-Baliviera et al., Arch. Surg. 124(12), 1400–1405 (1989)}.

TNFα appears to be involved in bone resorption diseases, including arthritis. When activated, leukocytes will produce bone-resorption, an activity to which the data suggest TNFα contributes. {Bertolini et al., Nature 319, 516–518 (1986) and Johnson et al., Endocrinology 124(3), 1424–1427 (1989).} TNFα also has been shown to stimulate bone resorption and inhibit bone formation in vitro and in vivo through stimulation of osteoclast formation and activation combined with inhibition of osteoblast function. Although TNFα may be involved in many bone resorption diseases, including arthritis, the most compelling link with disease is the association between production of TNFα by tumor or host tissues and malignancy associated hypercalcemia {Calci. Tissue Int. (US) 46(Suppl.), S3–10 (1990)}. In Graft versus Host Reaction, increased serum TNFα levels have been, associated with major complication following acute allogenic bone marrow transplants {Holler et al., Blood, 75(4), 1011–1016 (1990)}.

Cerebral malaria is a lethal hyperacute neurological syndrome associated with high blood levels of TNFα and the most severe complication occurring in malaria patients. Levels of serum TNFα correlated directly with the severity of disease and the prognosis in patients with acute malaria attacks {Grau et al., N. Engl. J Med. 320(24), 1586–1591 (1989)}.

Macrophage-induced angiogenesis TNFα is known to be mediated by TNFα. Leibovich et al. {Nature, 329, 630–632 (1987)} showed TNFα induces in vivo capillary blood vessel formation in the rat cornea and the developing chick chorioallantoic membranes at very low doses and suggest TNFα is a candidate for inducing angiogenesis in inflammation, wound repair, and tumor growth. TNFα production also has been associated with cancerous conditions, particularly induced tumors {Ching et al., Brit. J. Cancer, (1955) 72, 339–343, and Koch, Progress in Medicinal Chemistry, 22, 166–242 (1985)}.

TNFα also plays a role in the area of chronic pulmonary inflammatory diseases. The deposition of silica particles leads to silicosis, a disease of progressive respiratory failure caused by a fibrotic reaction. Antibody to TNFα completely blocked the silica-induced lung fibrosis in mice {Pignet et al., Nature, 344, 245–247 (1990)}. High levels of TNFα production (in the serum and in isolated macrophages) have been demonstrated in animal models of silica and asbestos induced fibrosis {Bissonnette et al., Inflammation 13(3), 329–339 (1989)}. Alveolar macrophages from pulmonary sarcoidosis patients have also been found to spontaneously release massive quantities of TNFα as compared with macrophages from normal donors {Baughman et al., J. Lab. Clin. Med. 115(1), 36–42 (1990)}.

TNFα is also implicated in the inflammatory response which follows reperfusion, called reperfusion injury, and is a major cause of tissue damage after loss of blood flow {Vedder et al., PNAS 87, 2643–2646 (1990)}. TNFα also alters the properties of endothelial cells and has various pro-coagulant activities, such as producing an increase in tissue factor pro-coagulant activity and suppression of the anticoagulant protein C pathway as well as down-regulating the expression of thrombomodulin {Sherry et al., J. Cell Biol. 107, 1269–1277 (1988)}. TNFα has pro-inflammatory activities which together with its early production (during the initial stage of an inflammatory event) make it a likely mediator of tissue injury in several important disorders including but not limited to, myocardial infarction, stroke and circulatory shock. Of specific importance may be TNFα-induced expression of adhesion molecules, such as intercellular adhesion molecule (ICAM) or endothelial leukocyte adhesion molecule (ELAM) on endothelial cells {Munro et al., *Am. J. Path.* 135(1), 121–132 (1989)}.

TNFα blockage with monoclonal anti-TNFα antibodies has been shown to be beneficial in rheumatoid arthritis {Elliot et al., *Int. J. Pharmac.* 1995 17(2), 141–145}. High levels of TNFα are associated with Crohn's disease {von Dullemen et al., *Gastroenterology*, 1995 109(1), 129–135} and clinical benefit has been achieved with TNFα antibody treatment.

Moreover, it now is known that TNFα is a potent activator of retrovirus replication including activation of HIV-1. {Duh et al., *Proc. Nat. Acad. Sci.* 86, 5974–5978 (1989); Poll et al., *Proc. Nat. Acad. Sci.* 87, 782–785 (1990); Monto et al., *Blood* 79, 2670 (1990); Clouse et al., *J. Immunol.* 142, 431–438 (1989); Poll et al., *AIDS Res. Hum. Retrovirus*, 191–197 (1992)}. AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T lymphocyte activation. Therefore, interference with cytokine activity such as by prevention or inhibition of cytokine production, notably TNFα, in an HIV-infected individual assists in limiting the maintenance of T lymphocyte caused by HIV infection.

Monocytes, macrophages, and related cells, such as kupffer and glial cells, also have been implicated in maintenance of the HIV infection. These cells, like T cells, are targets for viral replication and the level of viral replication is dependent upon the activation state of the cells. {Rosenberg et al., *The Immunopathogenesis of HIV Infection*, Advances in Immunology, 57 (1989)}. Cytokines, such as TNFα, have been shown to activate HIV replication in monocytes and/or macrophages {Poli et al., *Proc. Natl. Acad. Sci.*, 87, 782–784 (1990)}, therefore, prevention or inhibition of cytokine production or activity aids in limiting HIV progression for T cells. Additional studies have identified TNFα as a common factor in the activation of HIV in vitro and has provided a clear mechanism of action via a nuclear regulatory protein found in the cytoplasm of cells (Osborn, et al., *PNAS* 86 2336–2340). This evidence suggests that a reduction of TNFα synthesis may have an antiviral effect in HIV infections, by reducing the transcription and thus virus production.

AIDS viral replication of latent HIV in T cell and macrophage lines can be induced by TNFα {Folks et al., *PNAS* 86, 2365–2368 (1989)}. A molecular mechanism for the virus inducing activity is suggested by TNFα's ability to activate a gene regulatory protein (NFκB) found in the cytoplasm of cells, which promotes HIV replication through binding to a viral regulatory gene sequence (LTR) {Osborn et al., *PNAS* 86, 2336–2340 (1989)}. TNFα in AIDS associated cachexia is suggested by elevated serum TNFα and high levels of spontaneous TNFα production in peripheral blood monocytes from patients {Wright et al., *J. Immunol.* 141(1), 99–104 (1988)}. TNFα has been implicated in various roles with other viral infections, such as the cytomegalia virus (CMV), influenza virus, adenovirus, and the herpes family of viruses for similar reasons as those noted.

The nuclear factor κB (NFκB) is a pleiotropic transcriptional activator (Lenardo, et al., *Cell* 1989, 58, 227–29). NFκB has been implicated as a transcriptional activator in a variety of disease and inflammatory states and is thought to regulate cytokine levels including but not limited to TNFα and also to be an activator of HIV transcription (Dbaibo, et al., *J. Biol. Chem.* 1993, 17762–66; Duh et al., *Proc. Natl. Acad. Sci.* 1989, 86, 5974–78; Bachelerie et al., *Nature* 1991, 350, 709–12; Boswas et al., *J. Acquired Immune Deficiency Syndrome* 1993, 6, 778–786; Suzuki et al., *Biochem. And Biophys. Res. Comm.* 1993, 193, 277–83; Suzuki et al., *Biochem. And Biophys. Res Comm.* 1992, 189, 1709–15; Suzuki et al., *Biochem. Mol. Bio. Int.* 1993, 31(4), 693–700; Shakhov et al., *Proc. Natl. Acad. Sci. USA* 1990, 171, 35–47; and Staal et al., *Proc. Natl. Acad. Sci. USA* 1990, 87, 9943–47). Thus, inhibition of NFκB binding can regulate transcription of cytokine gene(s) and through this modulation and other mechanisms be useful in the inhibition of a multitude of disease states. The compounds described herein can inhibit the action of NFκB in the nucleus and thus are useful in the treatment of a variety of diseases including but not limited to rheumatoid arthritis, rheumatoid spondylitis, osteoarthritis, other arthritic conditions, septic shock, septis, endotoxic shock, graft versus host disease, wasting, Crohn's disease, ulcerative colitis, multiple sclerosis, systemic lupus erythrematosis, ENL in leprosy, HIV, AIDS, and opportuhistic infections in AIDS. TNFα and NFκB levels are influenced by a reciprocal feedback loop. As noted above, the compounds of the present invention affect the levels of both TNFα and NFκB.

Many cellular functions are mediated by levels of adenosine 3',5'-cyclic monophosphate (cAMP). Such cellular functions can contribute to inflammatory conditions and diseases including asthma, inflammation, and other conditions (Lowe and Cheng, *Drugs of the Future*, 17(9), 799–807, 1992). It has been shown that the elevation of cAMP in inflammatory leukocytes inhibits their activation and the subsequent release of inflammatory mediators, including TNFα and NFκB. Increased levels of cAMP also leads to the relaxation of airway smooth muscle. Phosphodiesterases control the level of cAMP through hydrolysis and inhibitors of phosphodiesterases have been shown to increase cAMP levels.

Decreasing TNFα levels and/or increasing cAMP levels thus constitutes a valuable therapeutic strategy for the treatment of many inflammatory, infectious, immunological or malignant diseases. These include but are not restricted to septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis, other arthritic conditions, Crohn's disease, ulcerative colitis, multiple sclerosis, systemic lupus erythrematosis, ENL in leprosy, radiation damage, and hyperoxic alveolar injury. Prior efforts directed to the suppression of the effects of TNFα have ranged from the utilization of steroids such as dexamethasone and prednisolone to the use of both polyclonal and monoclonal antibodies {Beutler et al., *Science* 234, 470–474 (1985); WO 92/11383}.

The compounds claimed in this patent inhibit the action of NFκB in the nucleus and thus are useful in the treatment of a variety of diseases including but not limited to rheumatoid arthritis, rheumatoid spondylitis, osteoarthritis, other arthritic conditions, septic shock, septis, endotoxic shock, graft versus host disease, wasting, Crohn's disease, ulcerative colitis, multiple sclerosis, systemic lupus erythrematosis, ENL in leprosy, HIV, AIDS, and opportunistic infections in AIDS.

It is not known at this time, however, how the compounds of the present invention regulate the levels of TNFα, NFκB, or both. As noted above, the compounds of the present invention affect the levels of both TNFα and NFκB.

The compounds can be used, under the supervision of qualified professionals, to inhibit the undesirable effects of TNFα or phosphodiesterase. The compounds can be administered orally, rectally, or parenterally, alone or in combination with other therapeutic agents including antibiotics, steroids, etc., to a mammal in need of treatment. Oral dosage forms include tablets, capsules, dragees, and similar shaped, compressed pharmaceutical forms. Isotonic saline solutions containing 20–100 milligrams/milliliter can be used for parenteral administration which includes intramuscular, intrathecal, intravenous and intra-arterial routes of administration. Rectal administration can be effected through the use of suppositories formulated from conventional carriers such as cocoa butter.

Dosage regimens must be titrated to the particular indication, the age, weight, and general physical condition of the patient, and the response desired but generally doses will be from about 1 to about 1000 milligrams/day as needed in single or multiple daily administration. In general, an initial treatment regimen can be copied from that known to be effective in interfering with TNFα activity for other TNFα mediated disease states by the compounds of the present invention. Treated individuals will be regularly checked for T cell numbers and T4/T8 ratios and/or measures of viremia such as levels of reverse transcriptase or viral proteins, and/or for progression of cytokine-mediated disease associated problems such as cachexia or muscle degeneration. If no effect is observed following the normal treatment regimen, then the amount of cytokine activity interfering agent administered is increased, e.g., by fifty percent a week.

The compounds of the present invention can also be used topically in the treatment or prophylaxis of topical disease states mediated or exacerbated by excessive TNFα production, such as viral infections, for example those caused by the herpes viruses or viral conjunctivitis, psoriasis, other skin disorders and diseases, etc.

The compounds can also be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anaemia virus, caprine arthritis virus, visna virus, and maedi virus, as well as other lentiviruses.

These compounds possess at least one center of chirality and thus will exist as optical isomers. Both the racemates of these isomers and the individual isomers themselves, as well as diastereoisomers when there are two or more chiral centers, are within the scope of the present invention. The racemates can be used as such or can be separated into their individual isomers mechanically as by chromatography using a chiral absorbent. Alternatively, the individual isomers can be prepared in chiral form or separated chemically from a mixture by forming salts with a chiral acid, such as the individual enantiomers of 10-camphorsulfonic acid, camphoric acid, alphabromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as to obtain either or both isomers substantially free of the other; i.e., in a form having an optical purity of >95%.

Prevention or inhibition of production of TNFα by these compounds can be conveniently assayed using methods known in the art. For example, TNFα Inhibition Assays can be performed as follows:

PBMC isolation: PBMC from normal donors were obtained by Ficoll-Hypaque density centrifugation. Cells were cultured in RPMI supplemented with 10% AB+ serum, 2 mM L-glutamine, 100 U/mL penicillin and 100 mg/mL streptomycin.

PBMC suspensions: Drugs were dissolved in DMSO (Sigma Chemical), further dilutions were done in supplemented RPMI. The final DMSO concentration in the presence or absence of drug in the PBMC suspensions was 0.25 wt %. Drugs were assayed at half-log dilutions starting at 50 mg/mL. Drugs were added to PBMC ($10^6$ cells/mL) in 96 wells plates one hour before the addition of LPS.

Cell stimulation: PBMC ($10^6$ cells/mL) in the presence or absence of drug were stimulated by treatment with 1 mg/mL of LPS from Salmonella Minnesota R595 (List Biological Labs, Campbell, Calif.). Cells were then incubated at 37° C. for 18–20 hours. Supernatants were then harvested and assayed immediately for TNFα levels or kept frozen at −70° C. (for not more than 4 days) until assayed.

TNFα Determination: The concentration of TNFα in the supernatant was determined by human TNFα ELISA kits (ENDOGEN, Boston, Mass.) according to the manufacturer's directions.

Another assay procedure utilizes plates (Nunc Immunoplates, Roskilde, D K) which are treated with 5 mg/mL of purified rabbit anti-TNFα antibodies at 4° C. for 12 to 14 hours. The plates then are blocked for 2 hours at 25° C. with PBS/0.05% Tween containing 5 milligrams/milliliter BSA. After washing, 100 mL of unknowns as well as controls are applied and the plates incubated at 4° C. for 12 to 14 hours. The plates are washed and assayed with a conjugate of peroxidase (horseradish) and mouse anti-TNFα monoclonal antibodies, and the color developed with o-phenylenediamine in phosphate-citrate buffer containing 0.012% hydrogen peroxide and read at 492 nm.

The compounds can be prepared using methods which are known per se. for example, a cyclic anhydride of lactone can be reacted with the appropriate amine:

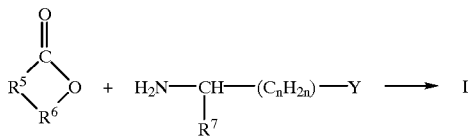

in which $R^5$, $R^6$, $R^7$, Y, and n are as defined above. The reaction can be effected analogously to the methods described in U.K. Patent Specification No. 1,036,694, the disclosure of which is incorporated herein by reference. Optionally acetic acid, with or without sodium acetate, can be added.

In place of the acid anhydride or lactone, one can utilize an N-carbethoxy derivative of the formula:

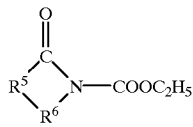

In a further embodiment, compounds in which $R^6$ is —$CH_2$— can be formed through condensation of a dialdehyde with a disubstituted aromatic compound in the presence of refluxing acetic acid utilizing the method of Griggs et al., *J. Chem. Soc. Chem. Comm.*, 1985, 1183–1184, the disclosure of which is incorporated herein by reference.

The disubstituted aromatic starting materials can be obtained through condensation of an appropriately substituted aldehyde and malonic acid, with intermediate formation of the amidine and subsequent decarboxylation.

The disubstituted aldehydes can be prepared utilizing classical methods for ether formation; e.g., reaction with the appropriate bromide in the presence of potassium carbonate. Numerous cycloalkyloxy benzaldehydes and procedures for preparing them are described in the literature. See, e.g., Ashton et al., *J. Med. Chem.*, 1994, 37, 1696–1703; Saccomano et al., *J. Med. Chem.*, 1994, 34, 291–298; and Cheng et al., *Org. and Med. Chem. Lett.*, 1995, 5(17), 1969–1972, the disclosures of which are incorporated herein by reference.

Typical compounds include 3-(1-oxobenzo[f]isoindol-2-yl)-3-(3-cyclopentyloxy-4-methoxyphenyl)propionic acid, 3-(1-oxobenzo[f]isoindol-2-yl)-3-(3-ethoxy-4-cyclohexyloxy-phenyl)propionic acid, 3-(1-oxobenzo[f]isoindol-2-yl)-3-(3-methoxy-4-ethoxyphenyl)propionic acid, 3-(1-oxobenzo[f]isoindol-2-yl)-3-(3,4-dimethoxyphenyl)propionic acid, 3-(1-oxo-benzo[f]isoindol-2-yl)-3-(3-ethoxy-4-cyclopentyloxyphenyl)propionic acid, 3-(1-oxo-4-azaisoindol-2-yl)-3-(3-methoxy-4-cyclopentyloxyphenyl)propionic acid, 3-(1-oxo-5-azaisoindol-2-yl)-3-(3-methoxy-4-cyclopentyloxyphenyl)propionic acid, 3-(1-oxo-4-azaisoindol-2-yl)-3-(3-ethoxy-4-cyclopentyloxyphenyl)propionic acid, 3-(1-oxo-4-azaisoindol-2-yl)-3-(3-methoxy-4-ethoxy-phenyl)propionic acid, 3-(1,3-dioxobenzo[f]isoindol-2-yl)-3-(3-cyclopentyloxy-4-cyclohexyloxyphenyl)propionamide, 3-(1,3-dioxobenzo[f]isoindol-2-yl)-3-(3-eth oxy-4-cyclohexyloxyphenyl)propionamide, 3-(1,3-dioxobenzo[f]isoindol-2-yl)-3-(3-methoxy-4-cyclobutyloxyphenyl)propionamide, 3-(1,3-dioxobenzo[f]isoindol-2-yl)-3-(3-methoxy-4-cyclopentyloxyphenyl)propionamide, 3-(1,3-dioxobenzo[f]isoindol-2-yl)-3-(3-methoxy-4-cyclopentyloxyphenyl)propionamide, 3-(1,3-dioxo-4-azaisoindol-2-yl)-3-(3-methoxy-4-cyclopentyloxyphenyl)propionamide, 3-(1,3-dioxo-5-azaisoindol-2-yl)-3-(3-methoxy-4-cyclopentyloxyphenyl)propionamide, 3-(1,3-dioxo-4-azaisoindol-2-yl)-3-(3-ethoxy-4-cyclopentyloxyphenyl)propionamide, 3-(1,3-dioxo-4-azaisoindol-2-yl)-3-(3-methoxy-4-cyclobutyloxyphenyl)propionamide, 3-(1-oxobenzo[f]isoindol-2-yl)-3-(3-cyclopentyloxy-4-cyclohexyloxyphenyl)propionic acid, 3-(1-oxobenzo[f]isoindol-2-yl)-3-(3-cyclopentyloxy-4-methoxyphenyl)propionamide, 3-(1-oxobenzo[f]isoindol-2-yl)-3-(3-ethoxy-4-cyclohexyloxyphenyl)propionamide, 3-(1-oxobenzo[f]isoindol-2-yl)-3-(3-methoxy-4-cyclopentyloxyl)propionamide, 3-(1-oxobenzo[f]isoindol-2-yl)-3-(3,4-dicyclopentyloxyphenyl)propionamide, 3-(1-oxobenzo[f]isoindol-2-yl)-3-(3,4-dicyclohexyloxyphenyl) propionamide, 3-(1-oxo-4-azaisoindol-2-yl)-3-(3-methoxy-4-cyclopentyloxyphenyl)propionamide, 3-(1-oxo-5-azaisoindol-2-yl)-3-(3-methoxy-4-cyclopentyloxyphenyl)propionamide, 3-(1-oxo-4-azaisoindol-2-yl)-3-(3-ethoxy-4-cyclopentyloxyphenyl)propionamide, 3-(1-oxo-4-azaisoindol-2-yl)-3-(3-cyclohexyloxy-4-ethoxyphenyl)propionamide, 3-(1,3-dioxobenzo[f]isoindol-2-yl)-3-(3-cyclopentyloxy-4-methoxyphenyl)propionic acid, 3-(1,3-dioxobenzo[f]isoindol-2-yl)-3-(3-ethoxy-4-cyclohexyloxyphenyl)propionic acid, 3-(1,3-dioxobenzo[f]isoindol-2-yl)-3-(3-methoxy-4-cyclohexyloxyphenyl)propionic acid, 3-(1,3-dioxobenzo[f]isoindol-2-yl)-3-(3,4-dicyclohexyloxyphenyl)propionic acid, 3-(1,3-dioxobenzo[f]isoindol-2-yl)-3-(3,4-dicyclopentyloxyphenyl)propionic acid, 3-(1,3-dioxo-4-azaisoindol-2-yl)-3-(3-methoxy-4-cyclopentyloxyphenyl)propionic acid, 3-(1,3-dioxo-5-azaisoindol-2-yl)-3-(3-methoxy-4-cyclopentyloxyphenyl)propionic acid, 3-(1,3-dioxo-4-azaisoindol-2-yl)-3-(3-ethoxy-4-cyclopentyloxyphenyl)propionic acid, 3-(1,3-dioxo-4-azaisoindol-2-yl)-3-(3-ethoxy-4-cyclopentyloxyphenyl)propionic acid, methyl 3-(1,3-dioxobenzo[f]isoindol-2-yl)-3-(3-cyclopentyloxy-4-methoxyphenyl)propionate, methyl 3-(1,3-dioxobenzo[f]isoindol-2-yl)-3-(3-ethoxy-4-cyclohexyloxyphenyl) propionate, methyl 3-(1,3-dioxobenzo[f]isoindol-2-yl)-3-(3-ethoxy-4-cyclopentyloxyphenyl)propionate, methyl 3-(1,3-dioxobenzo[f]isoindol-2-yl)-3-(3,4-dicyclopentyloxyphenyl)propionate, methyl 3-(1,3-dioxobenzo[f]isoindol-2-yl)-3-(3,4-dicyclohexyloxyphenyl) propionate, methyl 3-(1,3-dioxo-4-azaisoindol-2-yl)-3-(3-methoxy-4-cyclopentyloxyphenyl)propionate, methyl 3-(1,3-dioxo-5-azaisoindol-2-yl)-3-(3-methoxy-4-cyclopentyloxyphenyl)propionate, methyl 3-(1,3-dioxo-4-azaisoindol-2-yl)-3-(3-ethoxy-4-cyclopentyloxyphenyl) propionate, ethyl 3-(1,3-dioxobenzo[f]isoindol-2-yl)-3-(3-cyclopentyloxy-4-methoxyphenyl)propionate, ethyl 3-(1,3-dioxobenzo[f]isoindol-2-yl)-3-(3-ethoxy-4-cyclohexyloxyphenyl)propionate, ethyl 3-(1,3-dioxobenzo[f]isoindol-2-yl)-3-(3-methoxy-4-ethoxyphenyl)propionate, ethyl 3-(1,3-dioxobenzo[f]isoindol-2-yl)-3-(3,4-dimethoxyphenyl)propionate, ethyl 3-(1,3-dioxo-4-azaisoindol-2-yl)-3-(3-methoxy-4-cyclopentyloxyphenyl)propionate, ethyl 3-(1,3-dioxo-5-azaisoindol-2-yl)-3-(3-methoxy-4-cyclopentyloxyphenyl)propionate, ethyl and 3-(1,3-dioxo-4-azaisoindol-2-yl)-3-(3-ethoxy-4-cyclopentyloxyphenyl)propionate.

Representative aldehyde starting materials include 3-cyclopentyloxy4-methoxybenzaldehyde, 3-cyclopentyloxy-4-ethoxybenzaldehyde, 3-cyclohexyloxy-4-cyclohexyloxybenzaldehyde, 3-(exo-bicyclo[2.2.1]hept2-yloxy)-4-methoxybenzaldehyde, 3-(endo-bicyclo[2.2.1]hept-2-yloxy)-4-methoxybenzaldehyde, 3-(bicyclo[2.2.2]oct-2-yloxy)-4-methoxybenzaldehyde, 3-(bicyclo[3.2.1]oct-2-yloxy)-4-methoxybenzaldehyde, 3-indan-2-yloxy-4-methoxybenzaldehyde, and 3-(endo-benzobicyclo[2.2.1]hept-2-yloxy)-4-methoxybenzaldehyde.

The following examples will serve to further typify the nature of this invention but should not be construed as a limitation in the scope thereof, which scope is defined solely by the appended claims.

EXAMPLE 1

3-Amino-3-(3-cyclopentyloxy-4-methoxyphenyl) propionic Acid

A stirred suspension of 3-cyclopentyloxy-4-methoxybenzaldehyde (10.0 g, 45.4 mmol) and ammonium acetate (7.00 g, 90.8 mmol) in ethanol (95%, 30 mL) under nitrogen was heated to 45–50° C. and malonic acid (4.72 g, 45.4 mmol) was added. The solution was heated at reflux for 24 hours. A white solid precipitated, the mixture was allowed to cool to room temperature and was then filtered. The white solid was washed with ethanol, air dried and then dried in vacuo (60° C.,<1 mm) to afford 7.36 g (58%) of the product: mp 225–226° C.; $^1$H NMR (D$_2$O/NaOH/TSP) δ7.05–6.88 (m, 3H), 4.91–4.78 (m, 1H), 4.21–4.14 (m, 1H), 3.79 (s, 3H), 2.59–2.46 (m, 2H), 2.05–1.48 (m, 8H). Trace impurity peaks were present at 6.39 and 7.34 ppm. $^{13}$C NMR (D$_2$O/NaOD/TSP) δ182.9, 150.7, 149.1, 140.6, 121.6, 116.0, 114.9, 83.9, 58.5, 55.3, 49.8, 34.9, 26.3.

Similarly from equivalent amounts of 3-ethoxy-4-cyclopentyloxybenzaldehyde, 3-ethoxy-4-cyclohexyloxybenzaldehyde, 3-methoxy-4-cyclopentyloxybenzaldehyde, 3-methoxy-4-cyclohexyloxybenzaldehyde, 3-cyclohexyloxy-4-methoxybenzaldehyde, 3-cyclopentyloxy-4-ethoxybenzaldehyde, and 3-cyclohexyloxy-4-ethoxybenzaldehyde, there are respectively obtained according to the foregoin procedure 3-amino-3-(3-ethoxy-4-cyclopentyloxyphenyl)propionic acid, 3-amino-3-(3-ethoxy-4-cyclohexyloxyphenyl)propionic acid, 3-amino-3-(3-methoxy-4-cyclohexyloxyphenyl)propionic acid, 3-amino-3-(3-cyclopentyloxy-4-methoxyphenyl)propionic acid, 3-amino-3-(3-cyclohexyloxy)-4-methoxyphenyl)propionic acid, 3-amino-3-(3-cyclopentyloxy-4-ethoxyphenyl)propionic acid, and 3-amino-3-(3-cyclohexyloxy)-4-ethoxyphenyl)propionic acid.

EXAMPLE 2

3-Phthalimido-3-(3-cyclopentyloxy-4-methoxyphenyl)propionic Acid

To a stirred mixture of 3-amino-3-(3-cyclopentyloxy-4-methoxyphenyl)propionic acid (2.34 g, 8.40 mmol) and sodium carbonate (0.96 g, 9.05 mmol) in a mixture of water (20 mL) and acetonitrile (20 mL) under nitrogen was added N-carbethoxyphthalimide (1.9 g, 8.4 mmol). After 3 hours, the acetonitrile was removed in vacuo. The pH of the solution was adjusted to 1 with aqueous hydrogen chloride (4 N). Ether (5 mL) was added and the mixture stirred for 1 hour. The resulting slurry was filtered and the solid washed with water, air dried and then dried in vacuo (60° C.,<1 mm) to afford 2.92 g (85%) of the product as a white solid: mp 159–162° C.; $^1$H NMR (DMSO-d$_6$) δ12.40 (br s, 1H), 7.96–7.80 (m, 4H), 7.02 (s, 1H), 6.90 (s, 2H), 5.71–5.52 (m, 1H), 4.81–4.65 (m, 1H), 3.70 (s, 3H), 3.59–3.16 (m, 2H), 2.00–1.44 (m, 8H); $^{13}$C NMR (DMSO-d$_6$) δ171.7, 167.6, 149.1, 146.8, 134.6, 131.2, 131.1, 123.1, 119.4, 113.9, 112.1, 79.5, 55.5, 50.1, 36.1, 32.1, 32.1, 23.5; Anal. Calcd for C$_{23}$H$_{23}$NO$_6$. Theoretical: C, 67.47; H, 5.66; N, 3.42. Found: C, 67.34; H, 5.59; N, 3.14.

By substituting an equivalent amount of 2-carbethoxy-1,3-dioxobenzo[f]isoindoline in the foregoing procedure, there is obtained 3-(1,3-dioxobenzo[f]isoindolin-2-yl)-3-(3-cyclopentyloxy-4-methoxyphenyl)propionic acid. Likewise from 2-carbethoxy-1,3-dioxo-4-azaisoindoline and 2-carbethoxy-1,3-dioxo-5-azaisoindoline there are respectively obtained 3-(1,3-dioxo-4-azaindolin-2-yl)-3-(3-cyclopentyloxy-4-methoxyphenyl)propionic acid and 3-(1,3-dioxo-5-azaindolin-2-yl)-3-(3-cyclopentyloxy-4-methoxyphenyl)propionic acid.

1,3-Dioxobenzo[f]isoindoline, obtained from naphthalene-2,3-dicarboxylic acid anhydride through treatment with ammonia, is acylated as with ethyl chloroformate to yield 2-carbethoxy-1,3-dioxobenzo[f]isoindoline. Pyridine-2,3-dicarboxylic acid anhydride and pyridine-3,4-dicarboxylic acid anhydride are similarly converted to 2-carbethoxy-1,3-dioxo-4-azaisoindoline and 2-carbethoxy-1,3-dioxo-5-azaisoindoline.

Use in the procedure of this example of equivalent amounts of 2-carbethoxy-1,3-dioxobenzo[f]isoindoline with 3-amino-3-(3-ethoxy-4-cyclopentyloxyphenyl)propionic acid, 3-amino-3-(3-ethoxy-4-cyclohexyloxyphenyl)propionic acid, 3-amino-3-(3-methoxy-4-cyclohexyloxyphenyl)propionic acid, 3-amino-3-(3-cyclopentyloxy-4-methoxyphenyl)propionic acid, 3-amino-3-(3-cyclohexyloxy)-4-methoxyphenyl)propionic acid, 3-amino-3-(3-cyclopentyloxy-4-ethoxyphenyl)propionic acid, and 3-amino-3-(3-cyclohexyloxy)-4-ethoxyphenyl) propionic acid, all prepared as described in Example 1, yield 3-(1,3-dioxobenzo[f]isoindolin-2-yl)-3-(3-ethoxy-4-cyclopentyloxyphenyl)propionic acid, 3-(1,3-dioxobenzo[f]isoindolin-2-yl)-3-(3-ethoxy-4-cyclohexyloxyphenyl)propionic acid, 3-(1,3-dioxobenzo[f]isoindolin-2-yl)-3-(3-methoxy-4-cyclohexyloxyphenyl)propionic acid, 3-(1,3-dioxobenzo[f]isoindolin-2-yl)-3-(3-cyclopentyloxy-4-methoxyphenyl)propionic acid, 3-(1,3-dioxobenzo[f]isoindolin-2-yl)-3-(3-cyclohexyloxy)-4-methoxyphenyl) propionic acid, 3-(1,3-dioxobenzo[f]isoindolin-2-yl)-3-(3-cyclopentyloxy-4-ethoxyphenyl)propionic acid, and 3-(1,3-dioxobenzo[f]isoindolin-2-yl)-3-(3-cyclohexyloxy)-4-ethoxyphenyl)propionic acid, respectively.

Likewise by employing 2-carbethoxy-1,3-dioxo-4-azaisoindoline there are obtained from the same amines of Example 1 the compounds 3-(1,3-dioxo-4-azaindolin-2-yl)-3-(3-ethoxy-4-cyclopentyloxyphenyl)propionic acid, 3-(1,3-dioxo-4-azaindolin-2-yl)-3-(3-ethoxy-4-cyclohexyloxyphenyl)propionic acid, 3-(1,3-dioxo-4-azaindolin-2-yl)-3-(3-methoxy-4-cyclohexyloxyphenyl)propionic acid, 3-(1,3-dioxo-4-azaindolin-2-yl)-3-(3-cyclopentyloxy-4-methoxyphenyl)propionic acid, 3-(1,3-dioxo-4-azaindolin-2-yl)-3-(3-cyclohexyloxy)-4-methoxyphenyl)propionic acid, 3-(1,3-dioxo-4-azaindolin-2-yl)-3-(3-cyclopentyloxy-4-ethoxyphenyl)propionic acid, and 3-(1,3-dioxo-4-azaindolin-2-yl)-3-(3-cyclohexyloxy)-4-ethoxyphenyl)propionic acid.

Similarly from 2-carbethoxy-1,3-dioxo-5-azaisoindoline there are obtained with the amines of Example 1 the compounds 3-(1,3-dioxo-5-azaindolin-2-yl)-3-(3-ethoxy-4-cyclopentyl-oxyphenyl)propionic acid, 3-(1,3-dioxo-5-azaindolin-2-yl)-3-(3-ethoxy-4-cyclohexyloxyphenyl) propionic acid, 3-(1,3-dioxo-5-azaindolin-2-yl)-3-(3-methoxy-4-cyclohexyloxyphenyl)propionic acid, 3-(1,3-dioxo-5-azaindolin-2-yl)-3-(3-cyclopentyloxy-4-methoxyphenyl)propionic acid, 3-(1,3-dioxo-5-azaindolin-2-yl)-3-(3-cyclohexyloxy)-4-methoxyphenyl)propionic acid, 3-(1,3-dioxo-5-azaindolin-2-yl)-3-(3-cyclopentyloxy-4-ethoxyphenyl)propionic acid, and 3-(1,3-dioxo-5-azaindolin-2-yl)-3-(3-cyclohexyloxy)-4-ethoxyphenyl) propionic acid, respectively.

EXAMPLE 3

3-Phthalimido-3-(3-cyclopentyloxy-4-methoxyphenyl)propionamide

A mixture of 3-phthalimido-3-(3-cyclopentyloxy-4-methoxyphenyl)propionic acid (2.05 g, 5.00 mmol), 1,1'-carbonyldiimidazole (0.91 g, 5.5 mmol) and 4-dimethylaminopyridine (trace) in THF (20 mL) was stirred for 1.5 hours under nitrogen at approximately 25° C. To the solution was added ammonium hydroxide (1.07 mL, 16.0 mmol, 28–30%) and stirring was continued for 1.5 hours. A small amount of solid precipitated during this time. The mixture was concentrated to half its volume and a white solid precipitated. The mixture was filtered, washed with a small amount of THF, air dried and dried in vacuo (60° C.,<1 mm) to afford 1.27 g of the crude product. The crude product was purified by flash column chromatography (silica gel, 5% MeOH/CH$_2$Cl$_2$) and the resulting white solid was dried in vacuo (60° C., <1 mm) to afford 1 g (49%) of the product: mp 165–166° C.; $^1$H NMR (CDCl$_3$) δ7.85–7.61 (m, 4H), 7.16–7.04 (m, 2H) 6.85–6.75 (m, 1H), 5.80 (dd, J=5.8, 10.4 Hz, 1H), 5.66 (br s, 1H), 5.54 (br s, 1H), 4.82–4.70 (m, 1H), 3.80 (s, 3H), 3.71 (dd, J=10.4, 15 Hz, 1H), 3.06 (dd, J=5.8, 15 Hz, 1H), 2.06–1.51 (m, 8H); $^{13}$C NMR (CDCl$_3$) δ171.8, 168.3, 149.8, 147.7, 133.9, 131.8, 131.3, 123.3, 119.9, 114.6, 111.8, 80.4, 56.0, 51.6, 37.9, 32.7, 24.1; Anal. Calcd for C$_{23}$H$_{24}$N$_2$O$_5$. Theoretical: C, 67.63; H, 5.92; N, 6.86. Found: C, 67.25; H, 5.76; N, 6.68.

Similarly from equivalent amounts of 3-(1,3-dioxobenzo[f]isoindolin-2-yl)-3-(3-cyclopentyloxy-4-methoxyphenyl) propionic acid, 3-(1,3-dioxo-4-azaindolin-2-yl)-3-(3-cyclopentyloxy-4-methoxyphenyl)propionic acid, 3-(1,3-dioxo-5-azaindolin-2-yl)-3-(3-cyclopentyloxy-4-methoxyphenyl)propionic acid, 3-(1,3-dioxobenzo[f]isoindolin-2-yl)-3-(3-ethoxy-4-cyclopentyloxyphenyl) propionic acid, 3-(1,3-dioxobenzo[f]isoindolin-2-yl)-3-(3-ethoxy-4-cyclohexyloxyphenyl)propionic acid, 3-(1,3-dioxobenzo[f]isoindolin-2-yl)-3-(3-methoxy-4-cyclohexyloxyphenyl)propionic acid, 3-(1,3-dioxobenzo[f] isoindolin-2-yl)-3-(3-cyclopentyloxy-4-methoxyphenyl) propionic acid, 3-(1,3-dioxobenzo[f]isoindolin-2-yl)-3-(3-cyclohexyloxy)-4-methoxyphenyl)propionic acid, 3-(1,3)-dioxobenzo[f]isoindolin-2-yl-3-(3-cyclopentyloxy-4-ethoxyphenyl)propionic acid, 3-(1,3-dioxobenzo[f] isoindolin-2-yl)-3-(3-cyclohexyloxy)-4-ethoxyphenyl) propionic acid, 3-(1,3-dioxo-4-azaindolin-2-yl)-3-(3-ethoxy-4-cyclopentyloxyphenyl)propionic acid, 3(1,3-dioxo4-azaindolin-2-yl )-3)-(3-ethoxy-4-cyclohexyloxyphenyl)propionic acid, 3-(1,3-dioxo-4-azaindolin-2-yl)-3-(3-methoxy-4-cyclohexyloxyphenyl) propionic acid, 3-(1,3-dioxo-4-azaindolin-2-yl)-3-(3-cyclopentyloxy-4-methoxyphenyl)propionic acid, 3-(1,3-dioxo-4-azaindolin-2-yl)-3-(3-cyclohexyloxy)-4-methoxyphenyl)propionic acid, 3-(1,3-dioxo-4-azaindolin-2-yl)-3-(3-cyclopentyloxy-4-ethoxyphenyl)propionic acid, 3-(1,3-dioxo-4-azaindolin-2-yl)-3-(3-cyclohexyloxy)-4-ethoxyphenyl)propionic acid, 3-(1,3-dioxo-azaindolin-2-yl)-3-(3-ethoxy-4-cyclopentyloxyphenyl)propionic acid, 3(1,3-dioxo-azaindolin-2-yl)-3-(3ethoxy-cyclohexyloxyphenyl)propionic acid, 3-(1,3-dioxo-5-azaindolin-2-yl)-3-(3-methoxy-4-cyclohexyloxyphenyl) propionic acid, 3-(1,3-dioxo-5-azaindolin-2-yl)-3-(3-cyclopentyloxy-4-methoxyphenyl)propionic acid, 3-(1,3-dioxo-5-azaindolin-2-yl)-3-(3-cyclohexyloxy)-4-methoxyphenyl)propionic acid, 3-(1,3-dioxo-5-azaindolin-2-yl)-3-(3-cyclopentyloxy-4-ethoxyphenyl)propionic acid, and 3-(1,3-dioxo-5-azaindolin-2-yl)-3-(3-cyclohexyloxy)-4-ethoxyphenyl)propionic acid, there are respectively obtained according to the forgoing procedure 3-(1,3-dioxobenzo[f]isoindolin-2-yl)-3-(3-cyclopentyloxy-4-methoxyphenyl)propionamide, 3-(1,3-dioxo-4-azaindolin-2-yl)-3-(3-cyclopentyloxy-4-methoxyphenyl)propionamide, 3-(1,3-dioxo-5-azaindolin-2-yl)-3-(3-cyclopentyloxy-4-methoxyphenyl)propionamide, 3-(1,3-dioxobenzo[f] isoindolin-2-yl)-3-(3-ethoxy-4-cyclopentyloxyphenyl) propionamide, 3-(1,3-dioxobenzo[f]isoindolin-2-yl)-3-(3-ethoxy-4-cyclohexyloxyphenyl)propionamide, 3-(1,3-dioxobenzo[f]isoindolin-2-yl)-3-(3-methoxy-4-cyclohexyloxyphenyl)propionamide, 3-(1,3-dioxobenzo[f] isoindolin-2-yl)-3-(3-cyclopentyloxy-4-methoxyphenyl) propionamide, 3-(1,3-dioxobenzo[f]isoindolin-2-yl)-3-(3-cyclohexyloxy)-4-methoxyphenyl)propionamide, 3-(1,3-dioxobenzo[f]isoindolin-2-yl)-3-(3-cyclopentyloxy-4-ethoxyphenyl)propionamide, 3-(1,3-dioxobenzo[f] isoindolin-2-yl)-3-(3-cyclohexyloxy)-4-ethoxyphenyl) propionamide, 3-(1,3-dioxo-4-azaindolin-2-yl)-3-(3-ethoxy-4-cyclopentyloxyphenyl)propionamide, 3-(1,3-dioxo-4-azaindolin-2-yl)-3-(3-ethoxy-4-cyclohexyloxyphenyl)propionamide, 3-(1,3-dioxo-4-azaindolin-2-yl)-3-(3-methoxy-4-cyclohexyloxyphenyl) propionamide, 3-(1,3-dioxo-4-azaindolin-2-yl)-3-(3-cyclopentyloxy-4-methoxyphenyl)propionamide, 3-(1,3-dioxo-4-azaindolin-2-yl)-3-(3-cyclohexyloxy)-4-methoxyphenyl)propionamide, 3-(1,3-dioxo-4-azaindolin-2-yl)-3-(3-cyclopentyloxy-4-methoxyphenyl)propionamide, 3-(1,3-dioxo-4-azaindolin-2-yl)-3-(3-cyclohexyloxy)-4-ethoxyphenyl)propionamide, 3-(1,3-dioxo-5-azaindolin-2-yl)-3-(3-ethoxy-4-cyclopentyloxyphenyl)propionamide, 3-(1,3-dioxo-5-azaindolin-2-yl )-3-(3-ethoxy-4-cyclohexyloxyphenyl)propionamide, 3-(1,3-dioxo-5-azaindolin-2-yl)-3-(3-methoxy-4-cyclohexyloxyphenyl) propionamide, 3-(1,3-dioxo-5-azaindolin-2-yl)-3-(3-methoxy-4-methoxyloxyphenyl)propionamide, 3-(1,3-dioxo-5-azaindolin-2-yl)-3-(3-cyclopentyloxy-4-methoxyphenyl)propionamide 3-(1,3-dioxo-5-azaindolin-2-yl)-3-(3-cyclo hexyloxy)-4-methoxyphenyl)propionamide 3-(1,3-dioxo-5-azaindolin-2-yl)-3-(3-cyclopentyloxy -4-ethoxyphenyl)propionamide, and 3-(1,3-dioxo-5-azaindolin-2-yl)-3-(3-cyclohexyloxy)-4-ethoxyphenyl) propionamide.

EXAMPLE 4

Methyl 3-amino-3-(3-cyclopentyloxy-4-methoxyphenyl)propionate Hydrochloride

To a cooled (ice bath temperatures) and stirred mixture of 3-amino-3-(3-cyclopentyloxy-4-methoxyphenyl)propionic acid (3.00 g, 10.7 mmol) in methanol (20 mL) under nitrogen was added thionyl chloride (1.8 mL, 2.3 mmol) dropwise via syringe. The resulting solution was stirred at 0° C. for 1 hour, the ice bath was removed and stirring was continued at room temperature for 1 hour and a white solid precipitated. The methanol was removed and the solid was slurred in hexane. The mixture was filtered and the white solid was washed with hexane, air dried and then dried in vacuo (60° C., <1 mm) to afford 2.69 g (76%) of the product: mp 183–184.5° C.; $^1$H NMR (DMSO-d$_6$) δ8.76 (br s, 3H), 7.25 (s, 1H), 7.06–6.89 (m, 2H), 4.85–4.75 (m, 1H), 4.58–4.44 (m, 1H), 3.74 (s, 3H), 3.55 (s, 3H), 3.31–2.86 (m, 2H), 2.06–1.44 (m, 8H); $^{13}$C NMR (DMSO-d$_6$) δ169.1, 149.3, 146.5, 128.4, 119.5, 113.5, 111.4, 79.0, 55.0, 51.2, 50.3, 38.2, 31.7, 31.6, 23.0; Anal. Calcd for C$_{16}$H$_{24}$ClNO$_4$. Theoretical: C, 58.27; H, 7.33; N, 4.25. Found: C, 58.44; H, 7.34; N, 4.13.

Similarly prepared from 3-amino-3-(3-ethoxy-4-cyclopentyloxyphenyl)propionic acid, 3-amino-3-(3-ethoxy-4-cyclohexyloxyphenyl)propionic acid, 3-amino-3-(3-methoxy-4-cyclohexyloxyphenyl)propionic acid, 3-amino-3-(3-cyclopentyloxy-4-methoxyphenyl)propionic acid, 3-amino-3-(3-cyclohexyloxy)-4-methoxyphenyl) propionic acid, 3-amino-3-(3-cyclopentyloxy-4-ethoxyphenyl)propionic acid, and 3-amino-3-(3- cyclohexyloxy)-4-ethoxyphenyl)propionic acid are methyl 3-amino-3-(3-ethoxy-4-cyclopentyloxyphenyl)propionate, methyl 3-amino-3-(3-ethoxy-4-cyclohexyloxyphenyl) propionate, methyl 3-amino-3-(3-methoxy-4-cyclohexyloxy-phenyl)propionate, methyl 3-amino-3-(3-cyclopentyloxy-4-methoxyphenyl)propionate, methyl 3-amino-3-(3-cyclohexyloxy)-4-methoxyphenyl) propionate, methyl 3-amino-3-(3-cyclopentyloxy-4-ethoxyphenyl)propionate, and methyl 3-amino-3-(3-cyclohexyloxy)-4-ethoxyphenyl)propionate.

EXAMPLE 5

Methyl 3-phthalimido-3-(3-cyclopentyloxy-4-methoxyphenyl)propionate

To a stirred solution of methyl 3-amino-3-(3-cyclopentyloxy-4-methoxyphenyl)propionate hydrochloride (0.50 g, 1.52 mmol) and sodium carbonate (0.16 g, 1.52 mmol) in a mixture of water (5 mL) and acetonitrile (5 mL) under nitrogen was added N-carbethoxyphthalimide (0.34 g, 1.52 mmol). The solution was stirred for 3 hours at RT. The acetonitrile was removed in vacuo which afforded a two layer mixture which was extracted with $CH_2Cl_2$ (3×15 mL). The combined organic extracts were dried over $MgSO_4$, filtered and then concentrated in vacuo to afford 0.77 g of the crude product as an oil. The crude product was purified by flash column chromatography (silica gel, 35/65, ethyl acetate/hexane) the resulting glassy solid was dried in vacuo to afford 0.48 g (75%) of the product as a white solid: mp 76–78° C.; $^1$H NMR (CDCl$_3$) δ7.86–7.60 (m, 4H), 7.19–7.00 (m, 2H), 6.88–6.72 (m, 1H), 5.84–5.67 (m, 1H), 4.85–4.70 (m, 1H), 3.80 (s, 3H), 3.80–3.69 (m, 1H), 3.63 (s, 3H), 3.34–3.15 (m, 1H), 2.10–1.48 (m, 8H); $^{13}$C NMR (CDCl$_3$) δ171.0, 168.0, 149.8, 147.6, 133.9, 131.8, 130.9, 123.2, 120.1, 114.6, 111.7, 80.4, 55.9, 51.8, 50.7, 35.9, 32.7, 24.0; Anal. Calcd for $C_{24}H_{25}NO_6$. Theoretical: C, 68.03; H, 5.95; N, 3.31. Found: C, 67.77; H, 5.97; N; 3.20.

Similarly from equivalent amounts of 2-carbethoxy-1,3-dioxobenzo[f]isoindoline, 2-carbethoxy-1,3-dioxo-4-azaisoindoline, and 2-carbethoxy-1,3-dioxo-5-azaisoindoline for N-carbethoxyphthalimide, there are respectively obtained according to the forgoing procedure methyl 3-1,3-dioxobenzo[f]isoindolin-2-yl)-3-(3-cyclopentyloxy-4-methoxyphenyl)propionate, methyl 3-1,3-dioxo-4-azaindolin-2-yl)-3-(3-cyclopentyloxy-4-methoxyphenyl)propionate, and methyl 3-1,3-dioxo-5-azaindolin-2-yl)-3-(3-cyclopentyloxy-4-methoxyphenyl) propionate.

Use in the procedure of this example of equivalent amounts of 2-carbethoxy-1,3-dioxobenzo[f]isoindoline with methyl 3-amino-3-(3-ethoxy-4-cyclopentyloxyphenyl) propionate, methyl 3-amino-3-(3-ethoxy-4-cyclohexyloxyphenyl)propionate, methyl 3-amino-3-(3-methoxy-4-cyclohexyloxyphenyl)propionate, methyl 3-amino-3-(3-cyclopentyloxy-4-methoxyphenyl) propionate, methyl 3-amino-3-(3-cyclohexyloxy)-4-methoxyphenyl)propionate, methyl 3-amino-3-(3-cyclopentyloxy-4-ethoxyphenyl)propionate, and methyl 3-amino-3-(3-cyclohexyloxy)-4-ethoxyphenyl)propionate yields methyl 3-(1,3-dioxobenzo[f]isoindolin-2-yl)-3-(3-ethoxy-4-cyclopentyl-oxyphenyl)propionate, methyl 3-(1,3-dioxobenzo[f]isoindolin-2-yl)-3-(3-ethoxy-4-cyclohexyloxyphenyl)propionate, methyl 3-(1,3-dioxobenzo[f]isoindolin-2-yl)-3-(3-methoxy-4-cyclohexyloxyphenyl)propionate, methyl 3-(1,3-dioxobenzo[f]isoindolin-2-yl)-3-(3-cyclopentyloxy-4-methoxyphenyl)propionate, methyl 3-(1,3-dioxobenzo[f] isoindolin-2-yl)-3-(3-cyclohexyloxy)-4-methoxyphenyl) propionate, methyl 3-(1,3-dioxobenzo[f]isoindolin-2-yl)-3-(3-cyclopentyloxy-4-ethoxyphenyl)propionate, and methyl 3-(1,3-dioxobenzo[f]isoindolin-2-yl)-3-(3-cyclohexyloxy)-4-ethoxyphenyl)propionate.

Likewise by employing 2-carbethoxy-1,3-dioxo-4-azaisoindoline there are obtained from the same amines of Example 4 the compounds methyl 3-(1,3-dioxo-4-azaindolin-2-yl)-3-(3-ethoxy-4-cyclopentyloxyphenyl) propionate, methyl 3-(1,3-dioxo-4-azaindolin-2-yl)-3-(3-ethoxy-4-cyclohexyloxyphenyl)propionate, methyl 3-(1,3-dioxo-4-azaindolin-2-yl)-3-(3-methoxy-4-cyclohexyloxyphenyl)propionate, methyl 3-(1,3-dioxo-4-azaindolin-2-yl)-3-(3-cyclopentyloxy-4-methoxyphenyl) propionate, methyl 3-(1,3-dioxo-4-azaindolin-2-yl)-3-(3-cyclohexyloxy)-4-methoxyphenyl)propionate, methyl 3-(1, 3-dioxo-4-azaindolin-2-yl)-3-(3-cyclopentyloxy-4-ethoxyphenyl)propionate, and methyl 3-(1,3-dioxo-4-azaindolin-2-yl)-3-(3-cyclohexyloxy)-4-ethoxyphenyl) propionate.

Similarly from 2-carbethoxy-1,3-dioxo-5-azaisoindoline there are obtained with the amines of Example 4 the compounds methyl 3-(l,3-dioxo-5-azaindolin-2-yl)-3-(3-ethoxy-4-cyclopentyloxyphenyl)propionate, methyl 3-(1,3-dioxo-5-azaindolin-2-yl)-3-(3-ethoxy-4-cyclohexyloxyphenyl) propionate, methyl 3-(1,3-dioxo-5-azaindolin-2-yl)-3-(3-methoxy-4-cyclohexyloxyphenyl)propionate, methyl 3-(1, 3-dioxo-5-azaindolin-2-yl)-3-(3-cyclopentyloxy-4-methoxyphenyl)propionate, methyl 3-(1,3-dioxo-5-azaindolin-2-yl)-3-(3-cyclohexyloxy)-4-methoxyphenyl) propionate, methyl 3-(1,3-dioxo-5-azaindolin-2-yl)-3-(3-cyclopentyloxy-4-ethoxyphenyl)propionate, and methyl 3-(1,3-dioxo-5-azaindolin-2-yl)-3-(3-cyclohexyloxy)-4-ethoxyphenyl)propionate.

EXAMPLE 6

3-Amino-3-(3-{exobicyclo[2.2.1]hept-2-yloxy}-4-methoxyphenyl)propionic Acid

A stirred suspension of 3-(exobicyclo[2.2.1]hept-2-yloxy)-4-methoxybenzaldehyde (6.00 g, 24.4 mmol) and ammonium acetate (3.76 g, 48.8 mmol) in ethanol (95%, 20 mL) under nitrogen was heated to 45–50° C. and malonic acid (2.53 g, 24.4 mmol) was added. The solution was refluxed for 24 hours, allowed to cool to room temperature, and filtered. The solid was washed with ethanol, air dried, and dried in vacuo (60° C., <1 mm) to afford 3.17 g (43%) of the product: mp 225–226° C.; $^1$H NMR (D$_2$O/NaOD/TSP) δ7.09–6.90 (m, 3H), 4.41–4.28 (m, 1H), 4.27–4.15 (m, 1H), 3.82 (s, 3H), 2.64–2.48 (m, 2H) 2.44 (s, 1H), 2.31 (s, 1H), 1.92–1.76 (m, 1H), 1.69–1.38 (m, 4H), 1.30–1.05 (m, 3H).

EXAMPLE 7

Methyl 3-Amino-3-(3-{exobicyclo[2.2.1]hept-2-yloxy}-4-methoxyphenyl)propionate Hydrochloride To an ice bath cooled stirred suspension of 3-amino-3-(3-{exobicyclo[2.2.1]hept-2-yloxy}-4-methoxyphenyl) propionic acid (2.00 g, 6.55 mmol) in methanol (15 mL) under nitrogen was added thionyl chloride (1.56 mL, 13.1 mmol) dropwise via syringe. The resulting solution was stirred at 0° C. for 30 minutes, the ice bath was removed and stirring was continued at room temperature for 2.5 hours. The methanol was removed and the solid slurred in hexane (15 mL). The mixture was filtered and the white solid washed with hexane, air dried and then dried in vacuo (60° C., <1 mm) to afford 1.97 g (85%) of the product: mp 197.5–201.5° C.; $^1$H NMR (DMSO-d$_6$) δ7.50 (br s, 3H), 7.18 (s, 1H), 7.07–6.88 (m, 2H), 4.56–4.42 (m, 1H), 4.30–4.19 (m, 1H), 3.74 (s, 3H), 3.54 (s, 3H), 3.41–2.85 (m, 3H), 2.37 (s, 1H), 2.27 (s, 1H), 1.92–1.75 (m, 1H), 1.64–1.03 (m, 6H); $^{13}$C NMR (DMSO-d$_6$) δ169.4, 149.6, 146.4, 128.8, 120.0, 119.9, 113.8, 111.8, 80.1, 79.9, 55.5, 51.6, 50.7, 40.5, 39.2, 38.6, 34.8, 27.8, 23.7, 23.6.

EXAMPLE 8

Methyl 3-Phthalimido-3-(3-{exobicyclo[2.2.1]hept-2-yloxy}-4-methoxyphenyl)propionate To a stirred solution of methyl 3-amino-3-(3-{exobicyclo[2.2.1]hept-2-yloxy}-4-methoxyphenyl)propionate hydrochloride (1.00 g, 2.81 mmol) and sodium carbonate (0.3 g, 2.8 mmol) in a mixture of water (10 mL) and acetonitrile (10 mL) under nitrogen was added N-carbethoxyphthalimide (0.64 g, 2.81 mmol). The solution was stirred for 3 hours at room temperature. The acetonitrile was remove in vacuo and the residue extracted with methylene chloride (3×30 ml). The combined organic extracts were dried over MgSO$_4$, filtered and concentrated in vacuo to afford 1.44 g of the product, The product was further purified by flash column chromatography (silica gel, 20%, ethyl acetate/methylene chloride) to afford a white solid which was then dried in vacuo to afford 0.23 g (18%) of product: mp 47–48° C.; $^1$H NMR (CDCl$_3$) δ7.86–7.61 (m, 4H), 7.14–7.00 (m, 2H), 6.82–6.74 (m, 1H), 5.75 (dd, J=5.9, 10 Hz, 1H), 4.25–4.14 (m, 1H), 3.84–3.69 (m, 1H), 3.79 (s, 3H), 3.63 (s, 3H), 3.23 (dd, J=5.9, 16.5 Hz, 1H), 2.51–2.41 (m, 1H), 2.34–2.24 (m, 1H), 1.86–1.06 (m, 8H); $^{13}$C NMR (CDCl$_3$) δ171.1, 168.1, 149.7, 147.2, 133.9, 131.8, 130.9, 123.3, 120.1, 120.0, 114.5, 114.4, 111.8, 81.1, 56.0, 51.9, 50.8, 41.1, 41.0, 39.9, 39.8, 35.9, 35.5, 35.3, 28.4, 24.3; HPLC 97%; Anal. Calcd for C$_{26}$H$_{27}$NO$_6$. Theoretical: C, 69.47; H, 6.05; N, 3.12. Found: C, 69,22; H, 5.91; N, 2.95.

Similarly from equivalent amounts of 2-carbethoxy-1,3-dioxobenzo[f]isoindoline, 2-carbethoxy-1,3-dioxo-4-azaisoindoline, and 2-carbethoxy-1,3-dioxo-5-azaisoindoline for N-carbethoxyphthalimide, there are respectively obtained according to the forgoing procedure methyl 3-(1,3-dioxobenzo[f]isoindolin-2-yl)-3-(3-{exobicyclo[2.2.1]hept-2-yloxy}-4-methoxyphenyl)propionate, methyl 3-(1,3-dioxo-4-azaindolin-2-yl)-3-(3-{exobicyclo[2.2.1]hept-2-yloxy}-4-methoxyphenyl)propionate, and methyl 3-(1,3-dioxo-5-azaindolin-2-yl)-3-(3-{exobicyclo[2.2.1]hept-2-yloxy}-4-methoxyphenyl)propionamide.

EXAMPLE 9

3-Phthalimido-3-(3,4-diethoxyphenyl)propionitrile

To an ice bath cooled stirred suspension of 3-phthalimido-3-(3,4diethoxyphenyl)propionamide (0.96 g, 2.5 mmol), prepared for example as described in U.S. Pat. No. 5,463,063, and 4-methylmorpholine (0.66 mL, 6 mmol) in dimethylformamide (9 mL) under nitrogen, was added thionyl chloride (0.35 mL, 4.8 nimol) dropwise. There to was a slight exotherm after which the mixture was stirred at 0–5° C. for 30 minutes and at room temperature for 2 hours. The reaction was monitored by HPLC (Waters Nova-Pak/C-18 column, 3.9×150 mm, 4 micron, 1 mL/min, 240 nm, 50/50 acetonitrile/phosphoric acid 0.1% (aq)). The reaction mixture was poured into a mixture of sodium bicarbonate (8.5 mL) and ice (40 g) and stirred until the ice had melted. The mixture was filtered and the solid was washed with copious amounts of water. The wet solid was dissolved in methylene chloride (25 mL) and the organic layer was separated and dried over MgSO$_4$ and concentrated in vacuo to a sticky semi-solid. The solid was purified twice by flash column chromatography (silica gel, 3% ethyl acetate/methylene chloride) to afford a solid which was dried in vacuo (50° C., <1 mm) to afford 0.5 g (55%) of product as a pale yellow solid; $^1$H NMR (CDCl$_3$) δ7.91–7.65 (m, 4H), 7.12–6.98 (m, 2H), 6.90–6.78 (m, 1H), 5.61 (dd, J=6.4, 10.3 Hz, 1H), 4.19–3.96 (m, 4H), 3.83 (dd, J=10.3, 16.8 Hz, 1H), 3.26 (dd, J=6.4, 16.8 Hz, 1H), 1.55–1.30 (m, 6H); $^{13}$C NMR (CDCl$_3$) δ167.7, 149.2, 148.9, 134.3, 131.5, 129.1, 123.6, 120.2, 116.9, 113.2, 112.9, 64.7, 64.5, 51.1, 21.1, 14.7; HPLC 98.4%. Anal. Calcd for C$_{21}$H$_{20}$N$_2$O$_4$. Theoretical: C, 69.22; H, 5.53; N, 7.69. Found: C, 69.06; H, 5.48; N, 7.58.

Similarly obtained from 3-(1,3-dioxobenzo[f]isoindolin-2-yl)-3-(3-cyclopentyloxy-4-methoxyphenyl)propionamide, 3-(1,3-dioxo-4-azaindolin-2-yl)-3-(3-cyclopentyloxy-4-methoxyphenyl)propionamide, 3-(1,3-dioxo-5-azaindolin-2-yl)-3-(3-cyclopentyloxy-4-methoxyphenyl)propionamide, 3-(1,3-dioxobenzo[f]isoindolin-2-yl)-3-(3-ethoxy-4-cyclopentyloxyphenyl)propionamide, 3-(1,3-dioxobenzo[f]isoindolin-2-yl)-3-(3-ethoxy-4-cyclohexyloxyphenyl)propionamide, 3-(1,3-dioxobenzo[f]isoindolin-2-yl)-3-(3-methoxy-4-cyclohexyloxyphenyl)propionamide, 3-(1,3-dioxobenzo[f]isoindolin-2-yl)-3-(3-cyclopentyloxy-4-methoxyphenyl)propionamide, 3-(1,3-dioxobenzo[f]isoindolin-2-yl)-3-(3-cyclohexyloxy)-4-methoxyphenyl)propionamide, 3-(1,3-dioxobenzo[f]isoindolin-2-yl)-3-(3-cyclopentyloxy-4-ethoxyphenyl)propionamide, 3-(1,3-dioxobenzo[f]isoindolin-2-yl)-3-(3-cyclohexyloxy)-4-ethoxyphenyl)propionamide, 3-(1,3-dioxo-4-azaindolin-2-yl)-3-(3-ethoxy-4-cyclopentyloxyphenyl)propionamide, 3-(1,3-dioxo-4-azaindolin-2-yl)-3-(3-ethoxy-4-cyclohexyloxyphenyl)propionamide, 3-(1,3-dioxo-4-azaindolin-2-yl)-3-(3-methoxy-4-cyclohexyloxyphenyl)propionamide, 3-(1,3-dioxo-4-azaindolin-2-yl)-3-(3-cyclopentyloxy-4-methoxyphenyl)propionamide, 3-(1,3-dioxo-4-azaindolin-2-yl)-3-(3-cyclohexyloxy)-4-methoxyphenyl)propionamide, 3-(1,3-dioxo-4-azaindolin2-yl)-3-(3-cyclopentyloxy-4-ethoxyphenyl)propionamide, 3-(1,3-dioxo-4-azaindolin-2-yl)-3-(3-cyclohexyloxy)-4-ethoxyphenyl)propionamide, 3-(1,3-dioxo-5-azaindolin-2-yl)-3-(3-ethoxy-4-cyclopentyloxyphenyl)propionamide, 3-(1,3-dioxo-5-azaindolin-2-yl)-3-(3-ethoxy-4-cyclohexyloxyphenyl)propionamide, 3-(1,3-dioxo-5-azaindolin-2-yl)-3-(3-methoxy-4-cyclohexyloxyphenyl)propionamide, 3-(1,3-dioxo-5-azaindolin-2-yl)-3-(3-cyclopentyloxy-4-methoxyphenyl)propionamide, 3-(1,3-dioxo-5-azaindolin-2-yl)-3-(3-cyclohexyloxy)-4-methoxyphenyl)propionamide, 3-(1,3-dioxo-5-azaindolin-2-yl)-3-(3-cyclopentyloxy-4-ethoxyphenyl)propionamide, and 3-(1,3-dioxo-5-azaindolin-2-yl)-3-(3-cyclohexyloxy)-4-ethoxyphenyl)propionamide are 3-(1,3-dioxobenzo[f]isoindolin-2-yl)-3-(3-cyclopentyloxy-4-methoxyphenyl)propionitrile, 3-(1,3-dioxo-4-azaindolin-2-yl)-3-(3-cyclopentyloxy-4-methoxyphenyl)propionitrile, 3-(1,3-dioxo-5-azaindolin-2-yl)-3-(3-cyclopentyloxy-4-methoxyphenyl)propionitrile, 3-(1,3-dioxobenzo[f]isoindolin-2-yl)-3-(3-ethoxy-4-cyclopentyloxyphenyl)propionitrile, 3-(1,3-dioxobenzo[f]isoindolin-2-yl)-3-(3-ethoxy-4-cyclohexyloxyphenyl)propionitrile, 3-(1,3-dioxobenzo[f]isoindolin-2-yl)-3-(3-methoxy-4-cyclohexyloxyphenyl)propionitrile, 3-(1,3-dioxobenzo[f]isoindolin-2-yl)-3-(3-cyclopentyloxy-4-methoxyphenyl)

propionitrile, 3-(1,3-dioxobenzo[f]isoindolin-2-yl)-3-(3-cyclohexyloxy)-4-methoxyphenyl)propionitrile, 3-(1,3-dioxobenzo[f]isoindolin-2-yl)-3-(3-cyclopentyloxy-4-ethoxyphenyl)propionitrile, 3-(1,3-dioxobenzo[f]isoindolin-2-yl)-3-(3-cyclohexyloxy)-4-ethoxyphenyl)propionitrile, 3-(1,3-dioxo-4-azaindolin-2-yl)-3-(3-ethoxy-4-cyclopentyloxyphenyl)propionitrile, 3-(1,3-dioxo-4-azaindolin-2-yl)-3-(3-ethoxy-4-cyclohexyloxyphenyl)propionitrile, 3-(1,3-dioxo-4-azaindolin-2-yl)-3-(3-methoxy-4-cyclohexyloxyphenyl)propionitrile, 3-(1,3-dioxo-4-azaindolin-2-yl)-3-(3-cyclopentyloxy-4-methoxyphenyl)propionitrile, 3-(1,3-dioxo-4-azaindolin-2-yl)-3-(3-cyclohexyloxy)-4-methoxyphenyl)propionitrile, 3-(1,3-dioxo-4-azaindolin-2-yl)-3-(3-cyclopentyloxy-4-ethoxyphenyl)propionitrile, 3-(1,3-dioxo-4-azaindolin-2-yl)-3-cyclohexyloxy)-4-ethoxyphenyl)propionitrile, 3-(1,3-dioxo-5-azaindolin-2-yl)-3-(3-ethoxy-4-cyclopentyloxyphenyl)propionitrile, 3-(1,3-dioxo-5-azaindolin-2-yl)-3-(3-ethoxy-4-cyclohexyloxyphenyl)propionitrile, 3-(1,3-dioxo-5-azaindolin-2-yl)-3-(3-methoxy-4-cyclohexyloxyphenyl)propionitrile, 3-(1,3-dioxo-5-azaindolin-2-yl)-3-(3-cyclopentyloxy-4-methoxyphenyl)propionitrile, 3-(1,3-dioxo-5-azaindolin-2-yl)-3-(3-cyclohexyloxy)-4-methoxyphenyl)propionitrile, 3-(1,3-dioxo-5-azaindolin-2-yl)-3-(3-cyclopentyloxy-4-ethoxyphenyl)propionitrile, and 3-(1,3-dioxo-5-azaindolin-2-yl)-3-(3-cyclohexyloxy)-4-ethoxyphenyl)propionitrile.

EXAMPLE 10

3-Phthalimido-3-(3,4-dimethoxyphenyl)propionitrile

To an ice bath cooled stirred suspension of 3-phthalimido-3-(3,4-dimethoxyphenyl)propionamide (1.77 g, 5.00 mmol) and 4-methylmorpholine (1.3 mL, 12 mmol) in dimethylformamide (17 mL) under nitrogen, was added thionyl chloride (0.7 mL, 9.6 mmol) dropwise via a syringe. There was a slight exotherm and after 30 minutes, the cooling bath was removed and the reaction mixture was stirred for 2 hours at room temperature. The reaction mixture was poured into a mixture of sodium bicarbonate (17 g) and 75 mL of ice water and stirred until the ice had melted. The slurry was filtered and the solid was washed with copious amounts of water. The wet solid was dissolved in methylene chloride (50 mL) and the organic layer was separated, dried over sodium sulfate, and concentrated in vacuo to afford an orange solid. The solid was purified by flash column chromatography (silica gel, 5/95 ethyl acetate/methylene chloride, 50 mm id column) to afford 1.32 g (79%) of the product as a white solid: $^1$H NMR (CDCl$_3$) δ7.9–7.6 (m, 4H), 7.10 (m, 2H), 6.83 (m, 1 H), 5.64 (dd, J=6.5, 10.2 Hz, 1H), 3.88 (s, 3H), 3.85 (s, 3H), 3.82 (dd, 1H), 3.30 (dd, J=6.5, 16.8 Hz, 1 H); $^{13}$C NMR (CDCl$_3$) δ167.7, 149.5, 149.2, 134.4, 131.5, 129.1, 123.6, 120.1, 116.9, 111.1, 110.7, 56.0, 55.9, 51.1, 21.1. Anal. Calcd for C$_{19}$H$_{16}$N$_2$O$_4$0.18 H$_2$O. Theoretical: C, 76.2. H, 4.85; N, 8.25. Found: C, 67.23; H, 4.79; N, 8.27.

EXAMPLE 11

A stirred mixture 3-amino-3-phenylpropionic acid and cis-1,2-cyclohexanedicarboxylic anhydride in 10 mL of acetic acid under nitrogen was heated to reflux for 4 h and then allowed to cool to room temperature. The resulting mixture was concentrated to an orange yellow oil. This oil was crystallized from a 1/1 mixture of ethyl acetate/hexane to afford 1.77 g (58%) of 3-(cis-hexahydrophthalimido)-3-phenylpropionic acid as white crystals: $^1$H NMR (DMSO-d$_6$) δ12.45 (br s, 1 H, COOH), 7.33 (m, 5 H, Ph), 5.48 (dd, 1 H, J=6.3, 9.6, CH), 3.41 (dd, 1 H, J=16.5, 9.6 Hz), 3.14 (dd, 1H, J=16.5, 6.3 Hz), 2.50 (m, 2 H), 1.8–1.1 (m, 8 H); $^{13}$C NMR (DMSO-d$_6$) δ179.3, 179.2, 171.7, 138.7, 128.4, 127.5, 126.8, 50.1, 38.7, 38.6, 35.2, 23.0, 22.9, 21.1. Anal. Calcd for C$_{17}$H$_{19}$NO$_4$. Theory: C, 67.76; H, 6.36; N, 4.65. Found: C, 67.52; H, 6.20; N, 4.60.

EXAMPLE 12

A mixture of 3-(cis-hexahydrophthalimido)-3-phenylpropionic acid (0.903 g, 3.00 mmol) and carbonyldiimidazole (0.525 g, 3.75 mmol) in 13 mL of anhydrous tetrahydrofuran under nitrogen was stirred for 1 hour, then 0.25 mL of concentrated ammonium hydroxide was added to the reaction solution. After 20 minutes, the reaction mixture was concentrated in vacuo to an oil. The oil was diluted with 20 mL of water and the mixture extracted with ethyl acetate (20 mL). The organic layer was dried (sodium sulfate) and concentrated to afford an oil. The oil was then purified by flash chromatography (silica gel, 5/95 methanol/methylene chloride, R$_f$=0.3) to afford 210 mg of 3-(cis-hexahydrophthalimido)-3-phenylpropionamide as an oil which slowly crystallized to an ivory solid: $^1$H NMR (DMSO-d$_6$) d7.49 (s, 1 H, NH), 7.4–7.2 (m, 5 H, Ar), 6.90 (s, 1 H, NH), 5.54 (t, 1 H, J=7.8 Hz, CH), 3.09 (d, 2 H, J=7.8 Hz, CH2), 2.95–2.80 (m, 2 H, CH2), 1.8–1.1 (m, 8 H); $^{13}$C NMR (DMSO-d$_6$) δ179.6, 179.5, 171.5, 139.5, 128.6, 127.7, 127.2, 55.2, 50.6, 38.8, 36.5, 23.4, 23.3, 21.5

EXAMPLE 13

A stirred mixture of cis-5-norbonene-endo-2,3-dicarboxylic anhydride (1.64 g, 10.0 mmol) and 3-amino-3-phenylpropionic acid (1.65 g, 10.0 mmol) in 15 mL of acetic acid under nitrogen was heated to reflux for 6 hours. The resulting reaction solution was concentrated in vacuo to an oil which was crystallized from a 1/1 mixture of ethyl acetate/hexane to afford 2.03 g (65%) of 3-(cis-5-norbonene-endo-2,3-dicarboxylic imide)-3-phenylpropionic acid as a white powder: $^1$H NMR (DMSO-d$_6$) δ12.41 (br s, 1 H, COOH), 7.29 (m, 5 H, Ph), 6.0–5.7 (m, 2 H), 5.37 (t, 1 H, J=7.7 Hz), 3.5–3.1 (m, 6 H), 1.49 (m, 2 H); $^{13}$CNMR (DMSO-d$_6$) δ177.2, 177.1 171.4, 138.3, 134.3, 134.0, 128.1, 127.5, 127.1, 51.4, 50.1, 44.8, 44.5, 44.4, 35.1. Anal. Calcd for C$_8$H$_{17}$NO$_4$. Theory: C, 69.44; H, 5.50; N, 4.50. Found: C, 69.10; H, 5.33; N, 4.43.

EXAMPLE 14

A stirred suspension of 3-amino-3-(3,4-dimethoxyphenyl) propionic acid hydrochloride (0.689 g, 2.50 mmol) and 4-pyridyldicarboxylic acid anhydride (0.373 g, 2.50 mmol) in 20 mL of acetic acid was refluxed for overnight. The cooled reaction was filtered to remove a trace amount of solid and the filtrate concentrated to a thick yellow oil. The oil was diluted with 20 mL of ethyl acetate and heated to reflux and allowed to cool to room temperature. The resulting slurry was filtered and the filtrate concentrated to afford a yellow oil which was purified by flash chromatography (silica gel, 2/8 ethyl acetate/methylene chloride) to afford 0.592 g (64%) of methyl 3-(1,3-dioxo-5-azaisoindol-2-yl)-3-(3,4-dimethoxyphenyl )-propionate as a yellow oil which slowly solidified to afford a very pale yellow solid: $^1$H NMR (DMSO-d$_6$) δ8.15–7.75 (m, 8 H, Ar), 7.75–7.4 (m, 4 h, Ar and CONH), 9.13 (s, 1 H, Ar), 9.11 (d, 1 H, J=4.8 Hz), 7.90 (d, 1 H, J=4.8 Hz), 7.03 (s, 1 H), 6.93 (m, 2 H), 5.67 (overlapping dd, 1 H), 3.74 (s, 3 H), 3.73 (s, 3 H), 3.56 (s, 3 H), 3.65–3.30 (m, 2 H); $^{13}$C NMR (DMSO-d$_6$) δ170.7, 166.9, 166.5, 156.0, 148.6, 148.5, 144.1, 138.7, 130.4, 125.2, 119.1, 116.9, 111.6, 111.1, 55.4, 51.6, 50.1, 35.4.

EXAMPLE 15

Tablets, each containing 50 milligrams of active ingredient, can be prepared in the following manner:

| Constituents (for 1000 tablets) | |
|---|---|
| active ingredient | 50.0 grams |
| lactose | 50.7 grams |
| wheat starch | 7.5 grams |
| polyethylene glycol 6000 | 5.0 grams |
| talc | 5.0 grams |
| magnesium stearate | 1.8 grams |
| demineralized water | q.s. |

The solid ingredients are first forced through a sieve of 0.6 mm mesh width. The active ingredient, the lactose, the talc, the magnesium stearate and half of the starch then are mixed. The other half of the starch is suspended in 40 milliliters of water and this suspension is added to a boiling solution of the polyethylene glycol in 100 milliliters of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 16

Tablets, each containing 100 milligrams of active ingredient, can be prepared in the following manner:

| Constituents (for 1000 tablets) | |
|---|---|
| active ingredient | 100.0 grams |
| lactose | 100.0 grams |
| wheat starch | 47.0 grams |
| magnesium stearate | 3.0 grams |

All the solid ingredients are first forced through a sieve of 0.6 mm mesh width. The active ingredient, the lactose, the magnesium stearate and half of the starch then are mixed. The other half of the starch is suspended in 40 milliliters of water and this suspension is added to 100 milliliters of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 17

Tablets for chewing, each containing 75 milligrams of active ingredient, can be prepared in the following manner:

| Composition (for 1000 tablets) | |
|---|---|
| active ingredient | 75.0 grams |
| mannitol | 230.0 grams |
| lactose | 150.0 grams |
| talc | 21.0 grams |
| glycine | 12.5 grams |
| stearic acid | 10.0 grams |
| saccharin | 1.5 grams |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. The active ingredient, the glycine and the saccharin are carefully mixed, the mannitol, the lactose granulate, the stearic acid and the talc are added and the whole is mixed thoroughly and compressed to form tablets of approximately 10 nm diameter which are concave on both sides and have a breaking groove on the upper side.

EXAMPLE 18

Tablets, each containing 10 milligrams of active ingredient, can be prepared in the following manner:

| Composition (for 1000 tablets) | |
|---|---|
| active ingredient | 10.0 grams |
| lactose | 328.5 grams |
| corn starch | 17.5 grams |
| polyethylene glycol 6000 | 5.0 grams |
| talc | 25.0 grams |
| magnesium stearate | 4.0 grams |
| demineralized water | q.s. |

The solid ingredients are first forced through a sieve of 0.6 mm mesh width. Then the active ingredient, lactose, talc, magnesium stearate and half of the starch are intimately mixed. The other half of the starch is suspended in 65 milliliters of water and this suspension is added to a boiling solution of the polyethylene glycol in 260 milliliters of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 19

Gelatin dry-filled capsules, each containing 100 milligrams of active ingredient, can be prepared in the following manner:

| Composition (for 1000 capsules) | |
|---|---|
| active ingredient | 100.0 grains |
| microcrystalline cellulose | 30.0 grams |
| sodium lauryl sulphate | 2.0 grams |
| magnesium stearate | 8.0 grams |

The sodium lauryl sulphate is sieved into the active ingredient through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 milligrams each into size 0 (elongated) gelatin dry-fill capsules.

EXAMPLE 20

A 0.2% injection or infusion solution can be prepared, for example, in the following manner:

| active ingredient | 5.0 grams |
|---|---|
| sodium chloride | 22.5 grams |
| phosphate buffer pH 7.4 | 300.0 grams |
| demineralized water | qs 2500.0 milliliters |

The active ingredient is dissolved in 1000 milliliters of water and filtered through a microfilter or slurried in 1000 mL of $H_2O$. The buffer solution is added and the whole is made up to 2500 milliliters with water. To prepare dosage unit forms, portions of 1.0 or 2.5 milliliters each are introduced into glass ampoules (each containing respectively 2.0 or 5.0 milligrams of active ingredient).

What is claimed is:

1. A compound of the formula:

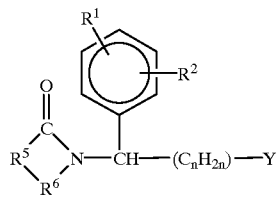

in which:
one of $R^1$ and $R^2$ is $R^3$—X— and the other is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkoxy, halo, or $R^3$—X—;

$R^3$ is monocycloalkyl of up to 10 carbon atoms, polycycloalkyl of up to 10 carbon atoms, or benzocyclic alkyl of up to 10 carbon atoms;

X is —$CH_2$— or —O—;

$R^5$ is a divalent pyrrolidine, imidazole, or thiophene ring in which the divalent bonds are on vicinal ring carbon atoms;

$R^6$ is —CO—, —$CH_2$—, —$CH_2CO$—, or —$SO_2$—;

Y is —CO[X]Z, —C≡N, —$OR^8$, alkyl of 1 to 5 carbon atoms, or aryl;

[X]Z is —$NH_2$, —OH, —NHR, —$R^9$, —$OR^9$, or alkyl of 1 to 5 carbon atoms;

$R^8$ is hydrogen or lower alkyl;

$R^9$ is alkyl or benzyl; and, n has a value of 0, 1, 2, or 3.

2. A compound according to claim 1 in which $R^6$ is —$SO_2$—.

3. A compound according to claim 1 which is a pure R—, a pure S— or an unequal mixture of R and S isomers.

4. A pharmaceutical composition comprising an amount of a compound according to formula I in claim 1 effective upon single or multiple dosage sufficient to inhibit phosphodiesterase III and phosphodiesterase IV or TNFα.

5. A method of inhibiting phosphodiesterase III and phosphodiesterase IV in a mammal with excessive levels of phosphodiesterase III and phosphodiesterase IV activity which comprises administering thereto an effective amount of a compound according to claim 1.

6. A method of inhibiting TNFα in a mammal with excessive levels of TNFα comprising administering thereto an effective amount of a compound of claim 1.

7. A method of treating in a mammal a inflammatory disease, which disease is sensitive to compounds according to claim 1, comprising administering thereto an effective amount of a compound according to claim 1.

8. A method of treating in a mammal a disease selected from the group consisting of arthritis, rheumatoid arthritis, osteoarthritis, reperfusion injury, inflammatory bowel disease, Crohn's disease, ulcerative colitis, systemic lupus erythrematosis, scleroderma, aphthous ulcers, graft versus host disease, asthma, chronic obstructive respiratory disease, adult respiratory distress syndrome, sarcoidosis, psoriasis, atopic dermatitis, endotoxemia and toxic shock syndrome, malaria, leprosy, cachexia, and acquired immune deficiency syndrome comprising administering a compound according to claim 1 to a patient in need thereof.

9. A method of treating a cancerous condition in a mammal selected form a group consisting of bladder cancer, glioblastoma, gliomas, astrocytoma, oligodendroglioma, breast, neuroendocrine, cholangiosarcoma, colorectal, head and neck, hepatocellular, chronic lymphocytic leukemia, acute myeloid leukemia, non-small cell lung carcinoma, mesothelioma, non-Hodgkins lymphoma, cutaneous B-lymphoma, cutaneous T-cell lymphoma, melanoma, multiple myeloma, myeloproliferative disease, myelodysplastic syndromes, ovarian, pancreatic, prostatic, renal cell carcinoma, and soft tissue sarcoma comprising administering to the mammal an effective amount of a compound according to claim 1.

* * * * *